United States Patent [19]
Lerman

[11] Patent Number: 5,941,859
[45] Date of Patent: Aug. 24, 1999

[54] WOUND IRRIGATION SHIELD WITH FLUID SCAVENGING

[76] Inventor: Benjamin S. Lerman, 5328 Bryant Ave., Oakland, Calif. 94618

[21] Appl. No.: 08/819,853

[22] Filed: Mar. 17, 1997

[51] Int. Cl.⁶ .................................................. A61M 35/00
[52] U.S. Cl. ............................................ 604/289; 604/313
[58] Field of Search ....................... 604/187, 192, 604/268, 289, 296, 300, 312, 313, 315, 316, 35, 36, 119

[56] References Cited

U.S. PATENT DOCUMENTS

| | | |
|---|---|---|
| 517,274 | 3/1894 | Gollings . |
| 680,723 | 8/1901 | Maurer . |
| 3,574,239 | 4/1971 | Sollerud ............................. 604/289 |
| 4,573,975 | 3/1986 | Frist et al. ......................... 604/192 |
| 4,692,140 | 9/1987 | Olson ................................. 604/40 |
| 4,769,003 | 9/1988 | Stamler ............................. 604/39 |
| 4,898,588 | 2/1990 | Roberts ............................. 604/187 |
| 5,030,214 | 7/1991 | Spector ............................. 604/301 |
| 5,078,694 | 1/1992 | Wallace ............................. 604/192 |
| 5,224,940 | 7/1993 | Dann et al. ....................... 604/290 |
| 5,291,887 | 3/1994 | Stanley et al. ................... 128/637 |
| 5,496,290 | 3/1996 | Ackerman ......................... 604/268 |
| 5,547,376 | 8/1996 | Harrel ............................... 433/116 |
| 5,735,833 | 4/1998 | Olson ................................. 604/289 |

*Primary Examiner*—John G. Weiss
*Assistant Examiner*—David J. Cho

[57] ABSTRACT

A wound irrigation device designed for use with a standard syringe and suction trap comprises a shield (10) which incorporates an irrigation tube (12) and nozzle (14) to deliver fluid at high pressure to a wound. The shield protects the operator from splashback, and includes a suction tube (16) to scavenge effluent, thus preventing spillage back into the wound or onto the patient and environs. A portable lavage/suction unit (28) may be used with the irrigation shield to provide fluid under pressure for irrigation, or to provide anesthetic under higher pressure for wound infiltration.

18 Claims, 5 Drawing Sheets

FIG._9

WOUND IRRIGATION SHIELD WITH FLUID SCAVENGING

BACKGROUND

1. Field of the Invention

This invention relates to wound treatment, particularly to shield devices that protect medical personnel from patient body secretions that splash back during wound irrigation.

2. Discussion of the Prior Art

High-pressure irrigation (optimally 8 pounds per square inch) of traumatic wounds is widely recommended in the medical literature. It removes particulate matter, such as soil, as well as germs, both of which can increase the chances of wound infection. Such irrigation has generally been accomplished by the use of a syringe and hypodermic needle. Unfortunately, this recommendation is often ignored in practice because of the inconvenience and mess caused by irrigant fluid splashing back out of the wound. Moreover, this splash-back puts medical personnel and other bystanders at risk of infection when blood-borne germs (such as HIV or hepatitis) are sprayed about. These risks have been addressed in the past by the use of goggles, masks, gloves, gowns, and the like to protect the operator. But these solutions are expensive, cumbersome, and do not protect bystanders or other patients who might be in the area. Recently, a clear plastic shield has been marketed, bearing U.S. Pat. No. 4,769,003 to Stamler (1988) and sold under the trademark ZEROWET by Zerowet, Inc. of Palos Verdes, Calif. The Zerowet shield is designed to fit on the end of a syringe. Its central lumen produces a narrow jet of fluid without the need for a needle, eliminating the risk of an accidental needle-stick. Its shield contains the splashback, protecting the operator from contamination. The manufacturer states that the shield should be held in light contact with the wound edges. But this device has been criticized by many authorities, who point out that, when used as directed, the effluent irrigating fluid will necessarily re-enter the wound after reflecting off of the shield. Thus irrigation with this device may not only fail to remove germs and debris from within a wound, it may actually spread these noxious elements to previously uncontaminated areas, or even carry them from dirty intact skin at the wound margins into the wound itself. In an effort to overcome these limitations, many physicians use this device incorrectly, holding it several centimeters away from the skin. This results in inadequate access to the recesses of the wound, inadequate irrigant stream pressures, and a failure of the shield to fully contain the splashback.

U.S. Pat. No. 5,496,290, to Ackerman (1996), discloses a very similar device which is said to have the advantage of allowing the irrigation to take place at a shorter distance from the wound and at a greater angle of incidence to the wound site. However the shallowness of the concave shield will only increase the likelihood that effluent from the wound will reflect from the shield directly back into the wound.

Moreover, when the Zerowet shield or the Ackerman device is used, irrigant contaminated with blood and debris pours off the rim of the shield, as illustrated in FIG. 3 of Ackerman's patent. In practice, large volumes of bloody water spill onto the patient, the patient's clothing and bedclothes, the bed, and the floor. This necessitates the expenditure of time and materials to clean up after an irrigation, exposes staff and others to potentially infectious blood and secretions, and results in patients' dissatisfaction with their care.

Preparations such as positioning a basin or towel beneath the wound are often futile because the irregular shape of the human body often causes the effluent stream to drip in unexpected directions. Moreover, the wounded part often needs to be repositioned several times in order to amply irrigate it, making the positioning of basins and towels impractical.

U.S. Pat. Nos. 4,898,588 (1990) and 5,224,940 (1993) to Roberts and Dann, respectively, disclose shields which suffer from all the aforementioned disadvantages, as well as requiring the use of sharp needles with the accompanying risk of inadvertent needle-stick injury.

U.S. Pat. No. 4,692,140 to Olson entitled Lavage/Suction Tip With Dual Splash Shield (1987), discloses a device which includes concentric barrels terminating in a pair of flared shields; the inner barrel delivers irrigation to a surgical site and the outer barrel provides suction to remove the effluent. The first shield is pliable and fixed at the distal end of the barrels, while the second shield is rigid and can be moved to multiple positions along the barrel. The device is not designed for use with an ordinary syringe; thus it requires the purchase of a separate lavage/suction handpiece and appropriate pumps for use with it. While it may be suitable for use in the operating theater during joint replacement surgery (the only particular use mentioned explicitly in the patent), the design is unnecessarily complicated, making its cost prohibitive for routine use in the irrigation of minor wounds in an outpatient setting.

All the aforementioned devices suffer from the limitation that the irrigant is delivered through a single small aperture, greatly limiting the rate of fluid delivery and unnecessarily prolonging the time required to adequately irrigate a wound.

None of the aforementioned devices allows precise control of the pressure at which fluid is delivered. Because excessive pressures may cause needless tissue damage, and because low pressures may fail to remove small particles and germs, this is a significant disadvantage.

Finally, nearly all wounds need to be anesthetized prior to repair, if not prior to cleansing. None of the described devices is designed to deliver anesthetic at a precisely controlled volume or pressure in order to infiltrate a wound without the use of a needle. The use of a needle to deliver anesthetic has many disadvantages: it is frightening to most patients, especially children, and it creates the risk of inadvertent needle-stick injuries.

OBJECTS AND ADVANTAGES

Accordingly, a principal object of this invention is to provide an improved apparatus and method for irrigation of wounds, with effective scavenging of the irrigant fluid such that there is neither mess nor risk of cross-contamination with such dangerous germs as HIV or hepatitis.

Other objects of this invention are:

to overcome the disadvantage of other shields that urge contaminated effluent back into the wound, to overcome the disincentives to properly cleansing a wound and thereby to minimize the chances of wound infection with its attendant costs in physical suffering, medical bills, and malpractice litigation, to provide a tool which is inexpensive to manufacture and sterilize for single patient use, and which is easy to use, to provide a means for cleaning wounds which does not soil the clothing and belongings of a patient, and which is manifestly superior to the wound care which a patient could perform at home, and which consequently results in greater patient satisfaction, to allow the more rapid delivery of irrigant fluids at appropriate pressures such that the total time needed to irrigate a wound is reduced, and to obviate the operator fatigue attendant upon manual fluid delivery systems, and to allow needle-free infiltration of anesthetic into a wound as well as irrigation of that wound, using a single device.

Further objects and advantages will become apparent from a consideration of the following descriptions and accompanying drawings.

| REFERENCE NUMERALS IN DRAWINGS |
| --- |
| 10 - shield |
| 11 - fluid |
| 12 - irrigation tube |
| 14 - nozzle |
| 16 - suction tube |
| 18 - suction aperture |
| 20 - suction |
| 22 - vacuum break |
| 24 - irrigant tubing |
| 26 - suction tubing |
| 28 - lavage/suction unit |
| 30 - pressurized irrigant |
| 32 - bag of irrigant |
| 33 - proximal irrigant tubing |
| 34 - inflatable bladder |
| 36 - non-distensible housing |
| 38 - volume indicator |
| 40 - air pump |
| 42 - pressure relief valve |
| 44 - pressure gauge |
| 46 - bag of anesthetic |
| 47 - medication tubing |
| 48 - fluid source selector |
| 50 - suction source |
| 52 - suction regulator |
| 54 - thumb trigger |
| 56 - patient |
| 58 - wound |

SUMMARY

The present invention is a wound irrigation shield incorporating a nozzle for the ingress of an irrigant, and an aperture allowing for the irrigant to be evacuated by suction. A portable unit may be used in conjunction with this shield to provide irrigant or anesthetic fluid under variable pressure, and to provide the needed suction and a reservoir for the effluent.

Figures 1, 4, 5:
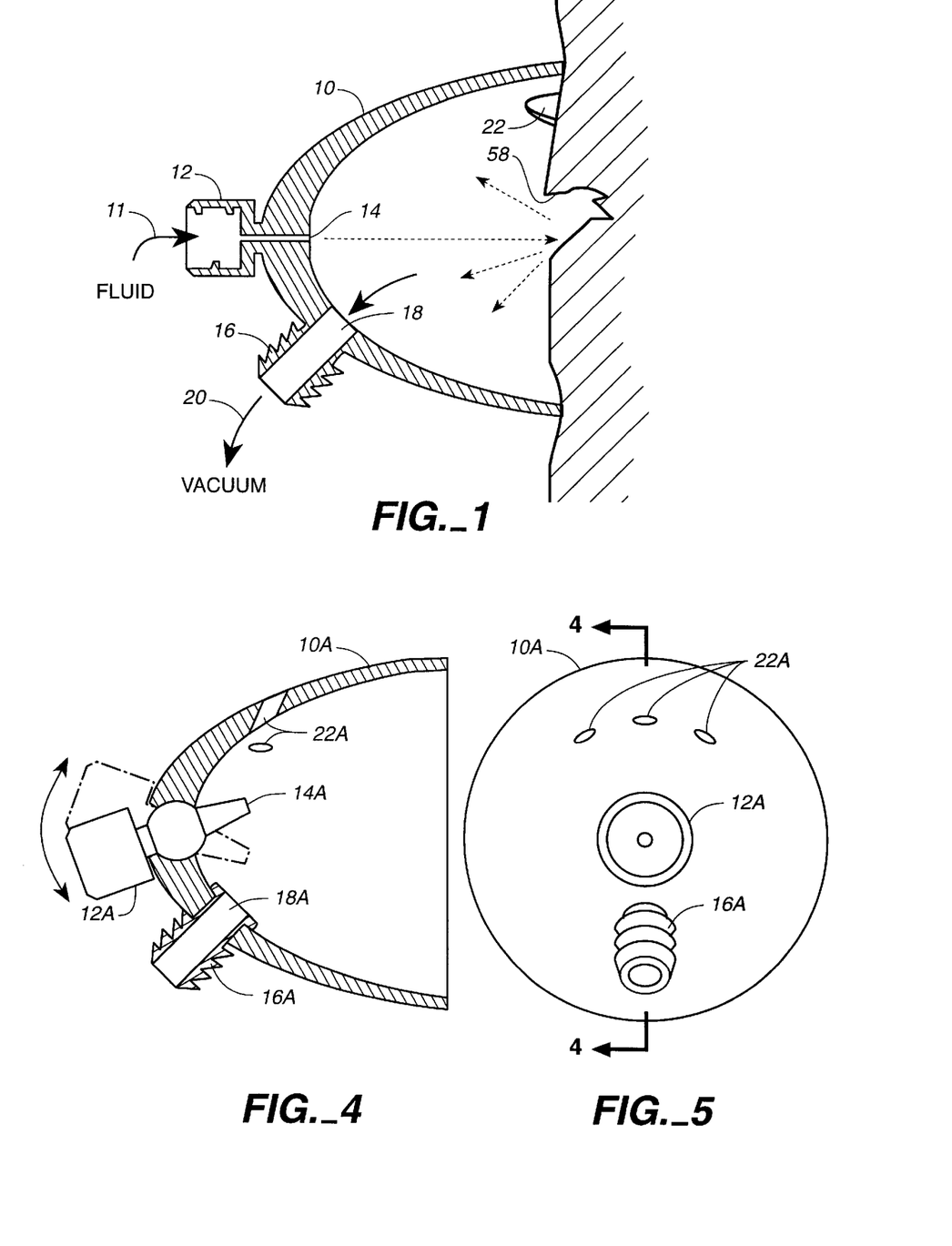
FIG. 1 shows a cross-sectional view of an irrigation shield in accordance with the invention being used on a wound.
FIGS. 4 and 5 show cross-sectional and perspective views of another embodiment of the irrigation shield with a swiveling nozzle.

DESCRIPTION—FIG. 1—MANUAL IRRIGATOR

FIG. 1 illustrates a cross section of a wound irrigation shield in contact with the skin around a wound 58. The wound irrigation shield comprises a shield or dome 10, which has the shape of a hemispheric, hollow dome, open at its base. Attached to the apex of shield 10 is an irrigation tube 12 which terminates in a nozzle 14. Irrigation tube 12 and nozzle 14 are circular, tubular structures.

Shield 10 also has a suction tube 16 which is fixed over a suction aperture 18 in the shield eccentric to the apex of the shield. The outer surface of suction tube 16 may be ridged.

The perimeter of the shield has a group of cutouts or vacuum breaks 22, shown as three in number, but fewer or more can be used. Vacuum breaks 22 and suction tube 16 are disposed approximately 180 degrees opposite each other around an imaginary symmetrical axis which passes through the apex of the shield.

The entire assembly described above is preferably made of transparent, substantially rigid plastic, such as PETG. The diameter of the perimeter of shield 10 is up to 10 cm but typically 4 cm. The total area of vacuum breaks 22 is typically 6 sq mm.

OPERATION—FIG. 1

To operate the wound irrigation device of FIG. 1, the operator (nurse, physician, or physician assistant) fills a standard luer-lock syringe (not shown) with irrigant and attaches it to the device by threading the syringe tip into irrigation tube 12. Then the operator frictionally inserts suction tube 16 into the end of a flexible tubing. He/She in turn is connects this flexible tubing to a source of suction (not shown) which incorporates a fluid trap as is routinely available in any medical facility (for example, Intermittent Suction Device by Ohio Medical Products of Cincinnati, Ohio).

The operator aims nozzle 14 at the portion of the wound which he/she wishes to irrigate, and advances the entire assembly toward the wound until some or all of the perimeter of the shield is in contact with the patient. The operator orients the assembly so that suction aperture 18 is at the lowest position which can be conveniently obtained. Vacuum breaks 22 prevent excessive suction from being applied to the wound itself and allow air to enter the shield so that there is greater air flow directed toward the suction tube.

The operator then manually applies vigorous pressure to the syringe plunger, forcing a stream of irrigant through the bore of irrigation tube 12 and nozzle 14 and out toward the wound at high pressure. This stream will then be reflected off of the wound back into the shield. However, rather than pouring off the shield edge and back into the wound or onto the patient, the irrigant will at this point be sucked through suction aperture 18 and thence through the bore of suction tube 18 and away to the fluid trap incorporated into suction source 50. The operator then detaches and refills the syringe and repeats the process as often as deemed necessary to cleanse the wound adequately.

Figure 2:
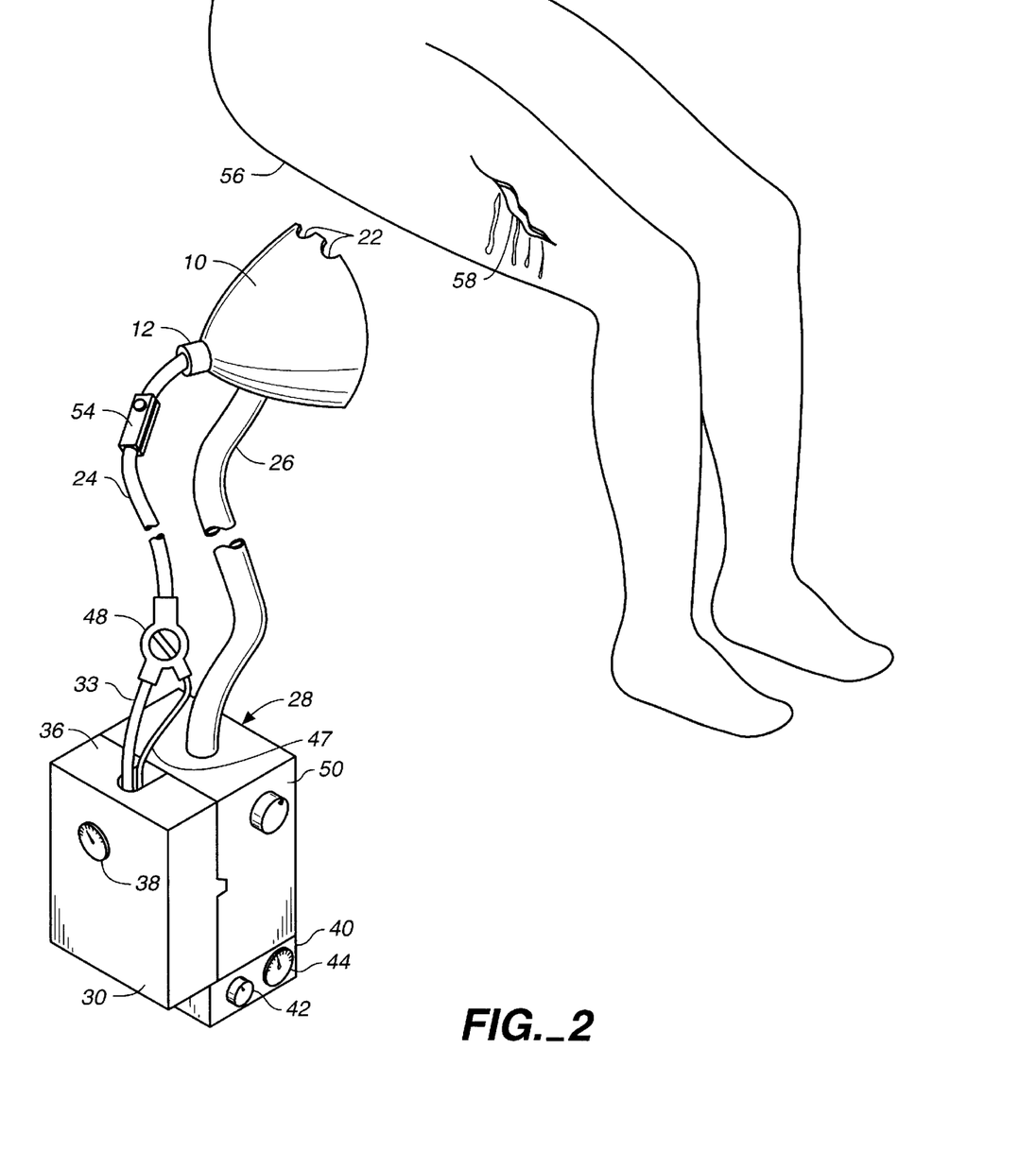
FIG. 2 shows a perspective drawing of the irrigation shield attached to a portable lavage/suction unit.
Figure 3:
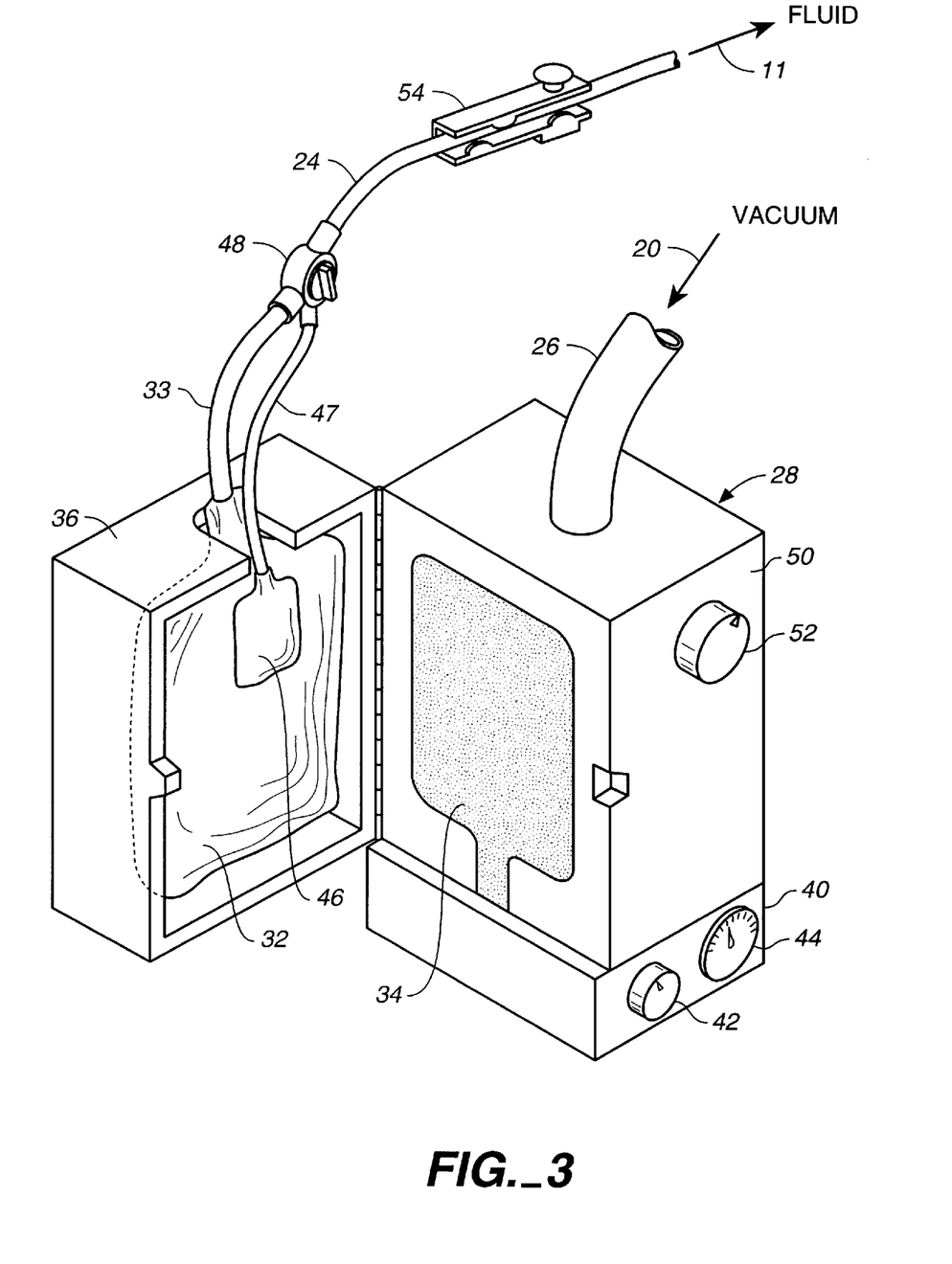
FIG. 3 shows the lavage/suction unit opened to reveal its mechanism for pressurizing fluids.

DESCRIPTION—FIGS. 2 AND 3—POWER IRRIGATOR

FIGS. 2 and 3 shows a complete power-driven wound irrigation system, comprising the shield of FIG. 2 connected to a portable lavage/suction unit 28.

Unit 28 consists of a source of pressurized irrigant fluid 30 and a source of vacuum 50. This source of pressurized irrigant fluid 30 consists of a standard disposable one liter plastic bag of a sterile saline solution 32 which, along with an inflatable bladder 34 is contained within a non-distensible housing 36. Inflatable bladder 34 is inflated by an electric air pump 40 which has an adjustable pressure relief valve 42 (range from 0 to 50 pounds per square inch) and a pressure gauge 44.

Fluid source 30 also includes a fluid source selector 48, a volume indicator 38, and a bag of anesthetic 46.

Unit 28 also contains a source of vacuum 50 which is connected to suction tube 16 by suction tubing 26. Vacuum source 50 has a suction regulator 52.

A thumb trigger 54 is present near the distal portion of irrigant tubing 24.

OPERATION—FIGS. 2 AND 3

To operate the device of FIG. 3, assume that the operator first wishes to anesthetize the wound. The operator fills a bag of anesthetic 46 with the desired dose of local anesthetic, e.g. 2% lidocaine, plus a specified volume which will be wasted in the irrigant tubing, and positions it as shown in the lavage/suction unit. The operator then selects the anesthetic fluid source using selector 48, and selects the appropriate pressure for needle-free infiltration of tissue with anesthetic using pressure relief valve 42 and pressure gauge 44.

The operator then positions the nozzle and shield over the wound 58 as described for FIG. 1. The operator then depresses thumb trigger 54, thus releasing the pressure on irrigant tubing 24 and allowing the anesthetic fluid to spray forcefully at the edge of the wound 58. The force of the stream of anesthetic causes it to infiltrate into the tissue.

By using a brief tap on thumb trigger 54 and then redirecting the shield, the operator can deliver a small dose of anesthetic at successive sites along the wound edge until the entire wound is anesthetized. The operator can then proceed with wound irrigation.

In order to irrigate a wound, the operator selects the irrigant fluid source using selector 48, and the desired pressure of irrigant using pressure relief valve 42 and pressure gauge 44. The operator then positions the nozzle and shield as described for FIG. 1, and depresses thumb trigger 54. A continuous stream of irrigant at the selected pressure flows from the tip of the nozzle. Continuous suction is provided to recover the effluent.

When the operator deems that the wound is adequately cleansed, the lavage/suction unit is turned off. The suction may be increased or decreased as needed during the procedure using suction regulator 52.

The total volume of fluid pumped can be read from the volume indicator 38, allowing precise documentation of the adequacy of wound cleansing, and/or documentation of the total amount of anesthetic used.

DESCRIPTION—FIGS. 4 TO 9—ALTERNATIVE SHIELD EMBODIMENTS

FIGS. 4 to 9 illustrate alternative embodiments of the wound irrigation shield.

FIGS. 4 and 5 show cross sectional and perspective drawings of an embodiment in which irrigation tube 16A has a spherical protrusion which is seated in a spherical hollow in the apex of shield 10A. Vacuum breaks 22A are tubular cutouts through the side walls of shield 10, oriented at an oblique angle away from the base of the dome.

Figure 6:
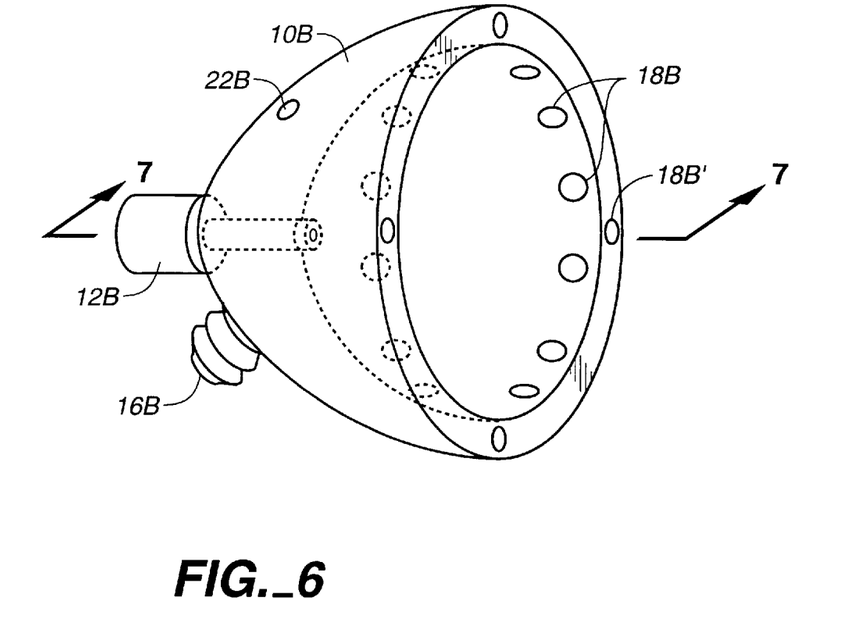
FIGS. 6 and 7 show perspective and cross-sectional views of still another embodiment which has suction apertures near and at the base of the shield.
Figure 7:
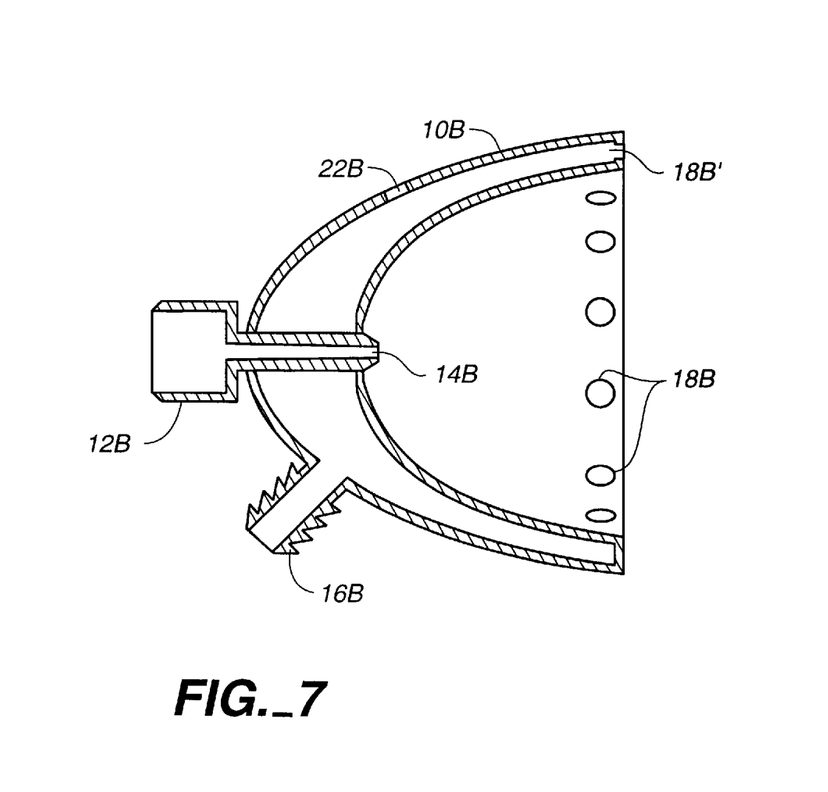

FIGS. 6 and 7 are perspective and cross-sectional views of another embodiment. Shield 10B comprises two concentric domes with a small gap between them, joined only at the perimeters of their bases. Suction apertures 18B are present along the side wall of the inner dome, near the perimeter of its base. Suction apertures 18B' are also present on the flat surface which joins the perimeters of the two domes. Vacuum break 22B is an aperture along the side wall of the outer dome, disposed 180 degrees opposite suction tube 16B around an imaginary symmetric axis which passes through the apex of the shield. Nozzle 14B is contiguous with irrigation tube 12B pierces the apices of both domes such that it penetrates slightly into the interior of the inner dome.

Figure 8:
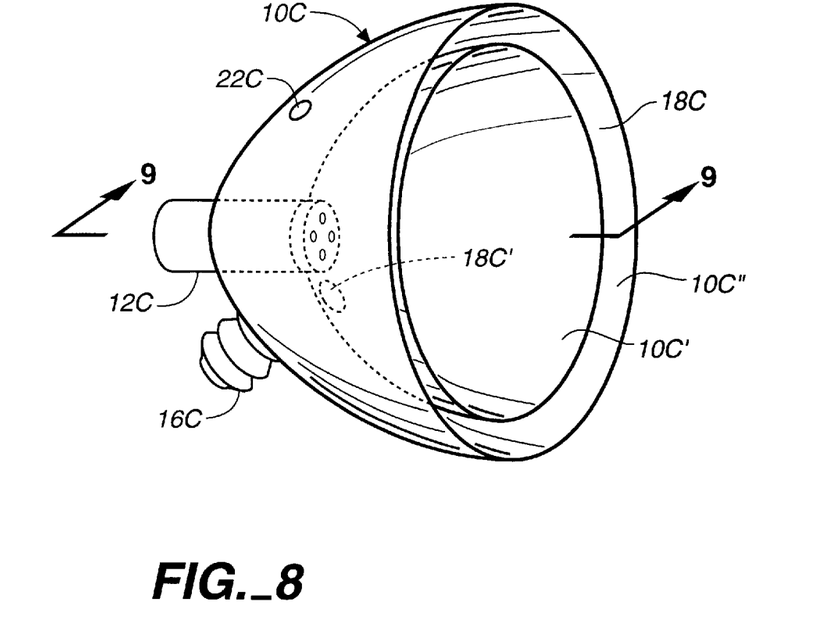
FIGS. 8 and 9 show perspective and cross-sectional drawings of yet another shield embodiment which has suction at the entire perimeter of its base. This figure also illustrates a nozzle with a plurality of apertures.
Figure 9:
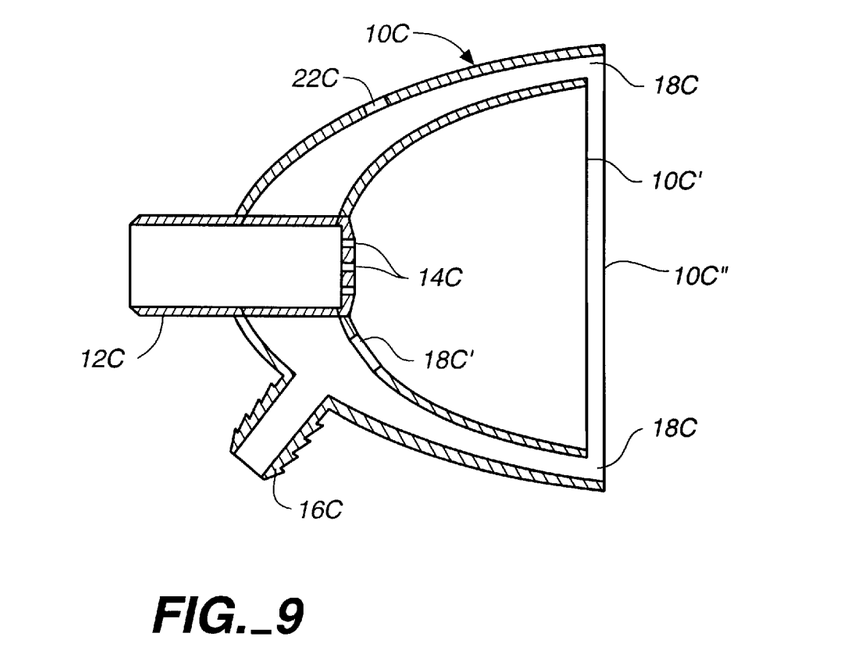

FIGS. 8 and 9 are perspective and cross-sectional views of another embodiment. Shield 10C comprises two concentric domes: a smaller inner dome 10C' and a larger outer dome 10C". Nozzle 14C pierces the apices of both of these domes and protrudes into the interior of the inner dome.

The perimeter of inner dome 10C' is smaller in diameter than that of outer dome 10C". The plane defined by the perimeter of inner dome 10C' is also closer to the tip of Nozzle 14C than that of outer dome 10C". Suction aperture 18C consists of the narrow annular created by the difference in sizes of the two domes.

Suction aperture 18C' is present near the apex of the inner dome. Suction tube 16C pierces the outer dome directly opposite suction aperture 18C'. Vacuum break 22C is a hole in the side wall of the outer dome, 180 degrees opposite from suction tube 16C around an imaginary axis which passes through the apices of the two domes.

The tip of nozzle 14C has a plurality of apertures.

OPERATION—FIGS. 4 TO 9

These three alternative embodiments can be used in exactly the same fashion described for FIG. 1, in conjunction with a syringe and existing suction apparatus. They can also be used in conjunction with the portable lavage/suction unit exactly as described in FIGS. 2 and 3.

The embodiment of FIGS. 4 and 5 differs in that irrigation tube 12A exists in a ball and socket arrangement with shield 10A such the operator can redirect nozzle 14B toward any point under the shield.

The embodiment of FIGS. 8 and 9 allows a higher flow rate of irrigant fluid by virtue of the plurality of apertures in the tip of nozzle 14C.

SUMMARY, RAMIFICATIONS AND SCOPE

Thus the reader will see that the invention described will allow rapid, effective irrigation of wounds at optimal pressures, without the inconvenience or health hazard of contaminated effluent splashback or spillage. The wound irrigation shield is simple in its design and can be used with syringes and suction apparatus already present in every health-care facility, making it quite inexpensive.

Facilities treating large numbers of wounded patients will benefit from the added convenience and speed of irrigation afforded by using the irrigation shield in conjunction with the portable lavage/suction unit. The same unit may be used to infiltrate wounds with anesthetic without the use of a needle. This feature saves time, eliminates risk of inadvertent needle-stick injuries, and minimizes patient distress, greatly enhancing patient satisfaction.

In pediatric patients the present needle-free unit will in many cases eliminate the fear which necessitates the use of physical restraints or sedative drugs. Thus the expense of time, materials and significant risk of airway obstruction, respiratory failure and death associated with restraints and sedatives are eliminated.

While the above description contains many specificities, these should not be construed as limiting the scope of the invention but as merely providing illustrations of some of the presently preferred embodiments of this invention. For example, the irrigation shield can be formed with multiple vacuum breaks, or none at all. The shield can be made of any material, rigid or flexible; it can be larger, smaller, of a different shape such as a shallower or deeper dome, or a cone, etc.

The nozzle can be shortened or lengthened to protrude beyond the base of the shield, and the arrangement of its aperture or apertures can be varied to produce different irrigation patterns. The irrigation tube can be moved away from the apex of the dome to an eccentric location. It can also be designed to pivot, or to telescope in or out of the shield in order to allow greater access to the recesses of a wound.

The suction tube can be made larger, moved to other locations on the shield or even made concentric with the irrigation tube. Additional suction apertures can be provided anywhere on the shield. Suction tips can also be positioned beyond the edges of the shield or protruding into the wound itself.

The nozzle can be made integral with the irrigation tube. The irrigation tube can be made integral with the shield and/or with the irrigation tubing. The suction tube can be made integral with the shield and/or with the suction tubing.

The portable lavage/suction unit can be powered by mechanical means, such as a hand or foot pump, rather than electrical means. The irrigant can be supplied at a broader range of pressures, and many alternative pumping arrangments can be used, such as a pinch roller. The anesthetic can be supplied in other more convenient packaging, rather than a bag, such as a multi-dose vial, syringe, pressurized cartridge, etc. The thumb trigger can be replaced by any convenient hand or foot operated switch. The entire lavage/suction unit can be supplied in a colorful housing (such as an elephant with the tubing as the elephant's trunk) to make it attractive to children.

Thus the scope of the invention should be determined by the appended claims and their legal equivalents, rather than by the examples given.

I claim:

1. A wound irrigation device, comprising:
   (a) a shield having a hollow shape, said shield having an interior surface, an exterior surface, a perimeter, and an interior volume,
   (b) a tubular irrigation nozzle protruding into said interior of said shield, said nozzle extending in a predetermined direction from said interior surface into said interior volume, wherein said nozzle further comprises means for varying said predetermined direction and the degree of protrusion of said nozzle into said interior volume; and
   (c) at least one suction aperture at said perimeter of said shield, whereby said wound will be irrigated without splattering or dripping dangerously contaminated fluids.

2. The wound irrigating device of claim 1 further including at least one vacuum break comprising a cutout in said shield.

3. The wound irrigating device of claim 1 wherein said nozzle has a plurality of apertures.

4. The wound irrigating device of claim 1 wherein said shield is dome-shaped.

5. The wound irrigating device of claim 1 wherein:
   (a) said shield comprises a larger outer dome and a smaller, concentric inner dome, each having a perimeter so as to provide an annular gap between perimeters of said domes, and
   (b) said suction aperture comprises said annular gap between said perimeters of said domes.

6. The wound irrigating device of claim 1, further including a portable lavage/suction device comprising:
   (a) a source of irrigant fluid,
   (b) a flexible tubing connecting said fluid source to said irrigation nozzle,
   (c) a pump means for pumping a volume of said fluid under pressure through said tubing and into said irrigation nozzle, and
   (d) a flexible tubing connecting said suction aperture to a suction means,
   whereby said wound can be quickly and conveniently irrigated with copious quantities of fluid.

7. The wound irrigating and portable suction/lavage device of claim 6, further including an indicator means for continuously indicating a total volume of fluid pumped.

8. The wound irrigating and portable suction/lavage device of claim 6 wherein said pump means is equipped with a pressure control means, whereby the pressure at which said fluid is pumped can be selected.

9. The wound irrigating and portable suction/lavage device of claim 6, further including:
   (a) a source of liquid medication,
   (b) a second flexible tubing connecting said medication to said irrigation nozzle,
   (c) a second pump means for urging said medication under variable, specifiable pressure through said tubing and into said irrigation nozzle,
   (d) an indicator means for continuously indicating the total volume of fluid pumped, and
   (e) a switching means for switching between said medication and said irrigant fluid.

10. A wound-cleansing device, comprising:
    (a) a shield shaped to cover a predetermined area of a patient's integument and enclose said predetermined volume of space, wherein said shield further comprises an inner wall and an outer wall so as to provide a gap between said inner wall and said outer wall;
    (b) said shield having a perimeter where it contacts said integument;
    (c) a nozzle for conveying fluid to a wound on said predetermined area of said integument, said nozzle being attached to said shield and protruding into said predetermined volume, wherein said nozzle further comprises means for varying said predetermined direction and the degree of protrusion of said nozzle into said interior volume;
    (d) a suction aperture at said perimeter of said shield, and
    (e) effluent means connected to said suction aperture for conveying fluid, via said aperture, away from said predetermined volume, whereby a wound can be cleansed without the leakage of dangerously contaminated fluids and without the spread of contaminants from one part of a wound to another part of the wound.

11. The wound-cleansing device of claim 10, further including a plurality of said suction apertures at said perimeter of said shield, said effluent means being connected to said suction apertures for conveying fluid, via said apertures, away from said predetermined volume.

12. The wound-cleansing device of claim 10 further including at least one vacuum break comprising a cutout in said shield.

13. The wound-cleansing device of claim 10 wherein said nozzle has a plurality of apertures.

14. The wound-cleansing device of claim 10 wherein said shield is dome-shaped.

15. The wound-cleansing device of claim 10, further including a portable lavage/suction device comprising:

(a) a source of irrigant fluid, (b) a second flexible tubing connecting said fluid source to said irrigation nozzle, (c) a second pump means for urging a volume of said fluid to be pumped under pressure through said tubing and into said irrigation nozzle, and (e) a flexible tubing connecting said suction aperture to a suction means whereby said wound can be quickly and conveniently irrigated with copious quantities of fluid.

16. The wound-cleansing device of claim 15, further including an indicator means for continuously indicating a total volume of fluid pumped.

17. The wound-cleansing device of claim 15, wherein said pump means is equipped with a pressure control means, whereby the pressure at which said fluid is pumped can be selected.

18. The wound-cleansing device of claim 15, further including:

(a) a source of liquid medication (b) a flexible tubing connecting said medication to said irrigation nozzle, (c) a pump means for urging said medication under variable, specifiable pressure through said tubing and into said irrigation nozzle, (d) an indicator means for continuously indicating the total volume of fluid pumped, and (e) a switching means for switching between said medication and said irrigant fluid.

* * * * *